(12) United States Patent
Braslau

(10) Patent No.: US 9,896,532 B2
(45) Date of Patent: Feb. 20, 2018

(54) DEACTIVATION OF URUSHIOL AND METHOD OF TREATMENT AND PREVENTION OF CONTACT DERMATITIS

(71) Applicant: The Regents of the University of California, Oakland, CA (US)

(72) Inventor: Rebecca Braslau, Santa Cruz, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/398,427

(22) PCT Filed: May 1, 2013

(86) PCT No.: PCT/US2013/039162
§ 371 (c)(1),
(2) Date: Oct. 31, 2014

(87) PCT Pub. No.: WO2013/166218
PCT Pub. Date: Nov. 7, 2013

(65) Prior Publication Data
US 2015/0132811 A1    May 14, 2015

Related U.S. Application Data

(60) Provisional application No. 61/641,008, filed on May 1, 2012.

(51) Int. Cl.
| | | |
|---|---|---|
| *C08G 2/16* | (2006.01) | |
| *A61K 33/00* | (2006.01) | |
| *A61K 49/00* | (2006.01) | |
| *A61K 38/44* | (2006.01) | |
| *C07C 46/06* | (2006.01) | |

(52) U.S. Cl.
CPC ............ *C08G 2/16* (2013.01); *A61K 33/00* (2013.01); *A61K 38/44* (2013.01); *A61K 49/0006* (2013.01); *A61K 49/0017* (2013.01); *C07C 46/06* (2013.01)

(58) Field of Classification Search
CPC .......... C07C 46/06; C08G 2/16; A61K 33/00; A61K 38/44; A61K 49/0006; A61K 49/0017
See application file for complete search history.

(56) References Cited

U.S. PATENT DOCUMENTS

| | | | | |
|---|---|---|---|---|
| 4,259,318 A | * | 3/1981 | Duhe | ............... A61K 38/44 424/94.4 |
| 2008/0107742 A1 | | 5/2008 | Hare et al. | |
| 2008/0227861 A1 | | 9/2008 | Manion et al. | |

FOREIGN PATENT DOCUMENTS

WO     2009139864 A2    11/2009

OTHER PUBLICATIONS

Warrener et al., "Direct Formation of α-Dione blocks from o-Benzoquinone Cycloadditions and their Value in the Synthesis of Fused Quinoxalines, 1,10-Phenanthrolines and Pteridines," Synlett 1998(6) 590-592.*
Shen et al., "Iron- and Manganese-Catalyzed Autoxidation of Dopamine in the Presence of I-Cysteine: Possible Insights into Iron- and Manganese-Mediated Dopaminergic Neurotoxicity," Chem. Res. Toxicol. 1998, 11, 824-837.*
Habibi et al., "Synthesis of Novel Benzothiazinedione," Asian Journal of Chemistry, vol. 22, No. 9, 2010, 7039-7042.*
Jeon et al., "Laccase-catalysed oxidations of naturally occurring phenols: from in vivo biosynthetic pathways to green synthetic applications," Microbial Biotechnology, 2012, 5(3), 318-332.*
International Search Report for International Application No. PCT/US2013/039162, dated Aug. 22, 2013, 2 pages.

* cited by examiner

*Primary Examiner* — Pancham Bakshi
*Assistant Examiner* — Mark R Luderer
(74) *Attorney, Agent, or Firm* — Kilpatrick Townsend & Stockton LLP

(57) ABSTRACT

The invention herein disclosed provides for compositions, methods for synthesizing said compositions, and methods for using said compositions, wherein the compositions and methods may be used to bind to and/or deactivate a poison oak oil, such as urushiol. The compositions and methods can be used to treat and/or reduce an inflammatory reaction and/or hypersensitivity to natural compounds found in poison oak, poison ivy, poison sumac, mango, lac tree, cashew nut, and Asian lacquer.

6 Claims, 6 Drawing Sheets

DEACTIVATION OF URUSHIOL AND METHOD OF TREATMENT AND PREVENTION OF CONTACT DERMATITIS

RELATIONSHIP TO OTHER APPLICATIONS

This application claims priority to and benefits under 35 U.S.C. § 371 of International Patent Application Serial Number PCT/US2013/039162, filed 1 May, 2013, entitled "Deactivation of Urushiol and Method of Treatment and Prevention of Contact Dermatitis", which claimed the benefit under 35 U.S.C. § 119(e) of U.S. Provisional application Ser. No. 61/681,008 filed 1 May, 2012, entitled "Fluorescence Detection and Deactivation of Urushiol and Method of Treatment and Prevention of Contact Dermatitis", the contents of which are all incorporated by reference in their entirety into the present disclosure.

FIELD OF THE INVENTION

The invention provides compositions, kits, and methods of using the compositions and kits for detecting, deactivating, degrading, immunogenic compounds from poison oak and poison ivy that induce urushiol-induced contact dermatitis.

BACKGROUND

Urushiol-induced allergic contact dermatitis in the United States most commonly results from unexpected exposure to oils from plants in the sumac Family Anacardiaceae. Approximately 10 to 50 million Americans suffer from rashes resulting from exposure every year. In particular, the genus *Toxicodendron* species (which include Western and Eastern poison oak *T. diversilobum*, poison ivy *T. radicans*, and poison sumac or dogwood *T. vernix*) are distributed widely across North America. Other sources of urushiol include poison wood (in Florida and the Bahamas), and the sap (kiurushi) of the Asian lacquer tree (*Toxicodendron verniciflua*) used as a varnish in Japanese lacquer ware, and cashew nut shells. (See, for example, Tucker and Swan (1998) New Engl. J. Med., 339(4): 235.)

Reaction to urushiol is an immunological response to the bio-oxidized form of urushiol (the orthoquinone). Approximately 50-70% of the U.S. population is either allergic to urushiol, or will become allergic to it upon sensitization by repeated exposure. Symptoms of allergic contact dermatitis from urushiol exposure (often referred to as *Rhus* dermatitis) vary from a mild annoyance to weeks of irritation and pain. Occasionally, exposure can lead to nephropathy and even to fatal systemic anaphylaxis. The monetary cost due to worker disability from urushiol-induced injuries is substantive: in the states of California, Washington, and Oregon, it has been estimated that up to one third of forestry workers are temporarily disabled by poison oak dermatitis each year. In California, the medical costs associated with poison oak injuries accounts for up to 1% of the annual workers' compensation budget. It has been estimated that *Toxicodendron* dermatitis is responsible for 10% of the total U.S. Forest Services lost-time injuries. In 1988, NIOSH estimated that 1.07-1.65 million occupational skin injuries occurred yearly, with an estimated annual rate of 1.4 to 2.2 cases per 100 workers (8) the costs attributable to lost productivity, medical payments, and disability payments are very high. (See U.S. Centers for Disease Control; Leading work-related diseases and injuries—United States. MMWR, 1986 335: 561-563).

Chemically, urushiol is a name given to a collection of related compounds that are 3-substituted catechols (1,2-benenediols), in which the long hydrophobic chain is a linear $C_{15}$ or $C_{17}$ alkyl chain containing 0-4 degrees of cis unsaturation (FIG. 1). The catechols with two, three, and four carbon-carbon double bonds (2-4 degrees of unsaturation) seem to be the most virulent in eliciting an allergic response. Each of the different members of the *Toxicodendron* species contain mixtures of the $C_{15}$ or $C_{17}$ alkyl chains, with various degrees of unsaturation.

They all share the catechol functionality in common, and a long, greasy alkyl chain that facilitates migration into the skin. In addition to direct contact with the toxic plants, exposure commonly occurs by transfer from animal fur, contaminated clothing, garden tools, fire-fighting equipment, forestry and sports equipment. There are a few commercially available products that can be applied prophylactically to protect the skin by creating a physical barrier using organoclays (for example, a lotion containing quaternium-18 bentonite is commercially available as IVYBLOCK from Enviroderm Pharmaceuticals, Inc.). However, the success of this strategy requires advanced planning. By far the majority of allergic contact dermatitis cases from urushiol result from unexpected exposure.

A number of methods to treat poison ivy or poison oak have been investigated, including hyposensitization, but this process is involved and can have unfavorable side effects. Studies towards an immunological approach to desensitization have been pursued, but have not yet reached a level of practical application. The best treatment to date is to avoid contact with urushiol. There are many recommended methods to remove urushiol after recent contact, including water, soapy water, organic solvents, and a variety of commercially available solubilizing mixtures including TECHNU, IVY-CLEANSE, ALL-STOP, ZANFEL (comprising fatty acid, alcohol, and the surfactant sodium lauroyl sarcosinate), and even DIAL ultra dishwashing soap. Thus the ability to deactivate urushiol before it transverses the skin will be extremely valuable in mitigating the suffering caused by contact with the various *Toxicodendron* species. In addition, continued re-exposure (chronic exposure) from repeated introduction of the oil to the patient (from door handles, shoelaces, etc.) is a considerable problem. As little as 0.001 mg of urushiol is enough to cause allergic contact dermatitis.

Treatment of the contact dermatitis usually involves a course of topical and/or enteric treatments with hydrocortisones, β-methasone, and other similar corticosteroids. Repeated exposure to either the original allergen or to a similar allergen can result in a severe hypersensitive immunoreaction, that is often extremely painful and, occasionally, fatal. There is therefore a particular need in the art for compounds and methods of treatment that can remove the allergen(s) prior to induction of an immune and/or allergic response, that can prevent the binding of the allergen(s) to an immunoglobulin or a cell-surface receptor, and/or that can be used to rapidly detect the presence of such allergen(s) so that other precautions may be used to remove the allergen(s) from the area of contact.

Of particular relevance is U.S. Pat. No. 8,389,232 B2, to Braslau et al., in which methods for detecting poison oak oil using boron compositions and nitroxides are disclosed. Another relevant publication is the fluorogenic chromatographic derivatization of catechols such as DOPA, and 2-aminophenols such as 3-hydroxytyrosine as taught by Stobaugh, using potassium ferricyanide and benzylamine to form benzoxazoles for HPLC-fluorescence detection. (See Pennington, J. P.; Schoneich, C.; Stobaugh, J. F., Selective fluorogenic derivatization with isotopic coding of catechols and 2-amino phenols with benzylamine: A chemical basis for the relative determination of 3-hydroxy-tyrosine and 3-nitro-tyrosine peptides. Chromatographia 2007, 66(9-10): 649-659). Daniel et al. (U.S. Pat. No. 5,320,946 A) teach a method and multilayer analytical element for the determination of catechol and catechol generating substances such as salicylate but do not teach that urushiol may be deactivated using the same process.

There is therefore a need in the art to provide for additional compositions and methods for detecting the presence of urushiol and/or deactivating urushiol from substrates, including, for example, skin and clothing, and from pets, for example, dogs, that may have contacted poison oak or the like.

BRIEF DESCRIPTION OF THE INVENTION

The invention is drawn to novel methods, kits, sprays (including aerosol sprays) and compositions for deactivating active compounds present in oils that are found in poison oak, poison ivy, poison sumac, Asian lacquer, and related plants, such as cashew nut. The methods disclosed herein may also be used to deactivate other catechols, both synthetic and those found in nature. The invention also is drawn to compositions that may be used to detect said active compounds using fluorescence. In one embodiment the methods of the invention may be used to deactivate catechols and alkyl-substituted catechols, such as, for example, urushiol, catechin, epicatechin, gallocatechin, epigallocatechin, epigallocatechin-3-gallate, and the like; and catecholamines, such as, for example, epinephrine, norepinephrine, dopamine, dihydroxyphenylalanine (DOPA), as well as phenols such as cardanol, and polyphenols, such as mangiferol, that are easily oxidized into catechols, and the like.

The invention provides methods for treating, deactivating and/or detecting the antigenic and/or allergenic compounds that induce urushiol-induced contact dermatitis. In one embodiment the method may be used for treating, deactivating, and/or detecting alk(en)yl catechols, and/or alk(en)yl resorcinols.

The invention may be used by clinicians, nursing staff, paramedics, emergency rescue team members, the military, firefighters, forestry personnel, lumberworkers, hunters, mountaineers, hikers, anglers, and the like. In one embodiment, the invention is a kit comprising the elements disclosed herein and a set of instructions of how to use the kit, wherein the kit is used for detecting, treating, and/or deactivating a catechol. The kit can be used, for example, in the home, in the field, in a camp, in a clinic, in a hospital, in an emergency room, and the like.

The invention provides a kit for deactivating a catechol, the kit comprising a vessel, the vessel shaped and adapted for confining a composition, the composition further comprising an oxidant, and an applicator. In one embodiment, the oxidant is a catalyst that uses air as the oxidant. In one preferred embodiment, the catalyst is a metal. In one more preferred embodiment, the catalyst is a nitroxide. In one alternative more preferred embodiment, the catalyst is a nitroxide precursor. In another alternative more preferred embodiment, the catalyst is an enzyme. In another alternative more preferred embodiment, the oxidant is a natural atmospheric gas. In another alternative more preferred embodiment, the oxidant is selected from the group consisting of bleach, sodium hypoclorite, potassium ferricyanide, hydrogen peroxide, hydroperoxide, dialkyl peroxide, thiourea-hydroperoxide complex, potassium monopersulfate, sodium dichloroisocyanurate, and other solid oxidizers. In one preferred embodiment, the metal catalyst is selected from the group consisting of iron, copper, cobalt, nickel, palladium, rhodium, ruthenium, manganese, and platinum. In one preferred embodiment, the nitroxide is selected from the group consisting of dialkyl nitroxide, alkyl, aryl nitroxide, Fremy's salt, and acyl nitroxide. In one preferred embodiment, the nitroxide is tetramethylpiperidinyloxy (TEMPO). In one preferred embodiment, the nitroxide or nitroxide precursor is a polymer-supported nitroxide, a polymer-supported amine or a polymer-supported hydroxamic acid. In one preferred embodiment, the enzyme is selected from the group consisting of an oxidase, a peroxidase, a laccase, a tyrosinase, and a xylanase. In one preferred embodiment, the natural atmospheric gas comprises oxygen. In one preferred embodiment, the applicator is a spray applicator. In another preferred embodiment, the applicator is a 'roll-on' applicator. In another preferred embodiment, the applicator is a brush applicator. In another preferred embodiment, the applicator is a gel applicator. In another preferred embodiment, the applicator is a pad or patch applicator. In one preferred embodiment, the kit comprises a lotion. In one preferred embodiment, the catechol is urushiol. In one preferred embodiment the kit further comprises an aerosol propellant. In one preferred embodiment, the kit further comprises a lamp. In one preferred embodiment, the lamp is a photon source, the photons having a wavelength of not more than 400 nm. In one preferred embodiment, the kit further comprises a free radical initiator. In one preferred embodiment, the free radical initiator is selected from the group consisting of an azo compound, a di-alkyl hyponitrite, and a peroxide.

In another preferred embodiment, the kit further comprises a chemical trap, wherein the chemical trap is selected from the group consisting of a Diels-Alder trap, an amine trap, and a thiol trap. In one more preferred embodiment, the Diels-Alder trap is selected from the group consisting of strained alkenes and electron-rich alkenes. In another more preferred embodiment, the amine trap is selected from the group consisting of secondary amine such as, but not limited to, 4-amino-2,2,6,6-tetramethylpiperidine-1-oxyl (4-amino-TEMPO), a primary amine such as, but not limited to, a lysine derivative, and an aryl amine, such as, but not limited to, aniline. In another more preferred embodiment, the amine trap is a polymer-supported amine. In another more preferred embodiment the thiol trap is selected from the group consisting of alkyl thiols and aryl thiols such as, but not limited to, a cysteine derivative, tert-dodecane thiol, derivatives of benzyl thiol, furan-2-ylmethanethiol, and derivatives of thiophenol. In another more preferred embodiment, the thiol trap is a polymer-supported thiol. In another more preferred embodiment, the chemical trap is selected from the group consisting of a diamine such as, but not limited to, 1,2-benzenediamine, ethylenediamine, and a polymer-supported diamine, alpha-amino ketone, and alpha-amino imine.

In a preferred embodiment, the invention provides a method for deactivating a catechol in a sample, the method comprising the steps of (i) contacting an oxidant with the sample (ii) allowing the oxidant to react with the catechol in the sample thereby creating an orthoquinone; (iii) allowing the orthoquinone to react with other urushiol molecules, thereby generating a polymer; the method resulting in deactivating the catechol in the sample. More preferably, the nitroxide is tetramethylpiperidinyloxy (TEMPO). In a yet alternative embodiment, the oxidant is a nitroxide plus oxidant. In a yet further alternative embodiment, the oxidant is an oxoammonium salt.

In another embodiment the method further comprising the steps of (iv) providing a free radical initiator, (v) allowing the catechol to react with the free radical initiator, thereby generating a semiquinone radical, (vi) allowing the semiquinone radical to auto-oxidize, or (vii) allowing the semiquinone to polymerize, the method resulting in deactivating the catechol, or (viii) allowing the semiquinone to further oxidise to orthoquinone. In an alternative preferred embodiment, the method further comprising the steps of (iv) providing a chemical trap, (v) allowing the orthoquinone to react with the chemical trap in the presence of the oxidant, the method resulting in deactivating the orthoquinone. In a more preferred embodiment, the chemical trap is selected from the group consisting of a Diels-Alder trap, an amine trap, a diamine trap, and a thiol trap. In a yet more preferred embodiment, the Diels-Alder trap is selected from the group consisting of strained alkenes and electron-rich alkenes. In another yet more preferred embodiment the amine trap is selected from the group consisting of 4-amino-2,2,6,6-tetramethylpiperidine-1-oxyl (4-amino-TEMPO). In another more preferred embodiment, the chemical trap is selected from the group consisting of a diamine such as, but not limited to, 1,2-benzenediamine, ethylenediamine, and a polymer-supported diamine, alpha-amino ketone, and alpha-amino imine. In a preferred embodiment, the catechol is selected from the group consisting of urushiol, catechin, cardanol, cardol, thrtsiol, epicatechin, gallocatechin, epigallocatechin, epigallocatechin-3-gallate, and catecholamines epinephrine, norepinephrine, dopamine, and dihydroxyphenylalanine (DOPA). In a more preferred embodiment, the catechol is urushiol.

In another preferred embodiment, the method further comprises wherein the chemical trap is selected from the group consisting of a Diels-Alder trap, an amine trap, and a thiol trap. In one more preferred embodiment, the Diels-Alder trap is selected from the group consisting of strained alkenes and electron-rich alkenes. In another more preferred embodiment, the chemical trap is a polymer-supported strained alkene or polymer-supported electron-rich alkene. In another more preferred embodiment, the amine trap is selected from the group consisting of secondary amine such as, but not limited to, 4-amino-2,2,6,6-tetramethylpiperidine-1-oxyl (4-amino-TEMPO), a primary amine such as, but not limited to, a lysine derivative, and an aryl amine, such as, but not limited to, aniline. In another more preferred embodiment, the amine trap is a polymer-supported amine. In another more preferred embodiment the thiol trap is selected from the group consisting of alkyl thiols and aryl thiols such as, but not limited to, cystein derivative, tert-dodecane thiol, derivatives of benzyl thiol, furan-2-ylmethanethiol, and derivatives of thiophenol. In another more preferred embodiment, the thiol trap is a polymer-supported thiol. In another more preferred embodiment, the chemical trap is selected from the group consisting of a diamine such as, but not limited to, 1,2-benzenediamine, ethylenediamine, and a polymer-supported diamine, alpha-amino ketone, and alpha-amino imine.

In another preferred embodiment the sample is selected from the group consisting of an area of a subject's skin, clothing, boots, pets, camping gear, tools, and outdoor equipment. In another preferred embodiment the sample is selected from the group consisting of a plant tissue, a plant extract, a plant tissue extract, an animal tissue, an animal extract, an animal tissue extract, and an animal fluid. In a more preferred embodiment the plant tissue is from a plant selected from the group consisting of poison oak, poison ivy, poison sumac, mango, lac tree, and Asian lacquer.

The invention further provides some methods as disclosed herein wherein the deactivation results in the formation of a fluorescent product, allowing detection as well as deactivation. In one embodiment the photon source is a lamp. In one more preferred embodiment the photons have a wavelength of not more than 600 nm. In a preferred embodiment the lamp is a hand-held lamp. In an alternative embodiment the photon source is the sun.

In a preferred embodiment of the invention the catechol is selected from the group consisting of urushiol, catechin, cardanol, cardol, thitsiol, epicatechin, gallocatechin, epigallocatechin, epigallocatechin-3-gallate, and catecholamines epinephrine, norepinephrine, dopamine, and dihydroxyphenylalanine (DOPA). In a more preferred embodiment the catechol is urushiol.

The invention provides for a pharmaceutical composition, the pharmaceutical composition comprising an oxidant composition. In another embodiment the pharmaceutical composition comprises an oxidant composition in an effective amount for the treatment of poison oak oil-induced contact dermatitis. In another more preferred embodiment, the oxidant is a natural atmospheric gas. In another alternative more preferred embodiment, the oxidant is selected from the group consisting of bleach, sodium hypochlorite, potassium ferricyanide, hydrogen peroxide, hydroperoxides, dialkyl peroxides, thiourea-hydroperoxide complex, potassium monopersulfate, sodium dichloroisocyanurate, and other solid oxidizers. In a preferred embodiment the poison oak oil comprises a catechol. In a more preferred embodiment the catechol is urushiol. In a most preferred embodiment the pharmaceutical composition comprises an oxidant in an effective amount for the deactivation of a catechol in poison oak oil.

In another preferred embodiment, the pharmaceutical composition further comprises a chemical trap, wherein the chemical trap is selected from the group consisting of a Diels-Alder trap, an amine trap, a thiol trap, and a diamine trap. In one more preferred embodiment, the Diels-Alder trap is selected from the group consisting of strained alkenes and electron-rich alkenes. In another more preferred embodiment, the Diels-Alder trap is a polymer-supported strained alkene or polymer-supported electron-rich alkene. In another more preferred embodiment, the amine trap is selected from the group consisting of secondary amine such as, but not limited to, 4-amino-2,2,6,6-tetramethylpiperidine-1-oxyl (4-amino-TEMPO), a primary amine such as, but not limited to, a lysine derivative, and an aryl amine, such as, but not limited to, aniline. In another more preferred embodiment, the amine trap is a polymer-supported amine. In another more preferred embodiment the thiol trap is selected from the group consisting of alkyl thiols and aryl thiols such as, but not limited to, a cysteine derivative, tert-dodecane thiol, derivatives of benzyl thiol, furan-2-ylmethanethiol, and derivatives of thiophenol. In another more preferred embodiment, the thiol trap is a polymer-supported thiol. In another more preferred embodiment, the chemical trap is selected from the group consisting of a diamine such as, but not limited to, 1,2-benzenediamine, ethylenediamine, and a polymer-supported diamine, alpha-amino ketone, and alpha-amino imine.

The invention provides a topical composition, the topical composition comprising an effective amount of an oxidant and a suitable excipient, carrier, or combination thereof. In another embodiment the topical composition optionally containing xanthan gum or gellan gum. In a more preferred embodiment the oxidant is present in an amount selected from the group consisting of from about 99.5% to about 0.001%, from about 95% to about 0.1%, and from about 90% to about 0.5%, by weight, based on the total combined weight of the oxidant thereof, not including other excipient, carrier, or combination thereof. In a most preferred embodiment the topical composition comprises an oxidant in an effective amount for the deactivation of a catechol in poison oak oil.

In another preferred embodiment, the topical composition further comprises a chemical trap, wherein the chemical trap is selected from the group consisting of a Diels-Alder trap, an amine trap, a diamine trap, and a thiol trap. In one more preferred embodiment, the Diels-Alder trap is selected from the group consisting of strained alkenes and electron-rich alkenes. In another more preferred embodiment, the Diels-Alder trap is a polymer-supported strained alkene or polymer-supported electron-rich alkene. In another more preferred embodiment, the amine trap is selected from the group consisting of secondary amine such as, but not limited to, 4-amino-2,2,6,6-tetramethylpiperidine-1-oxyl (4-amino-TEMPO), a primary amine such as, but not limited to, a lysine derivative, and an aryl amine, such as, but not limited to, aniline. In another more preferred embodiment, the amine trap is a polymer-supported amine. In another more preferred embodiment the thiol trap is selected from the group consisting of alkyl thiols and aryl thiols such as, but not limited to, a cysteine derivative, tert-dodecane thiol, derivatives of benzyl thiol, furan-2-ylmethanethiol, and derivatives of thiophenol. In another more preferred embodiment, the thiol trap is a polymer-supported thiol. In another more preferred embodiment, the chemical trap is selected from the group consisting of a diamine such as, but not limited to, 1,2-benzenediamine, ethylenediamine, and a polymer-supported diamine, alpha-amino ketone, and alpha-amino imine.

The invention further provides a topical medicament, the topical medicament comprising an oxidant and a suitable excipient, carrier, or combination thereof. In a more preferred embodiment the topical medicament comprises an oxidant in an effective amount for the deactivation of a catechol in poison oak oil to avoid induced contact dermatitis. In another more preferred embodiment the topical medicament comprises an oxidant in an effective amount for the treatment of poison oak oil-induced contact dermatitis.

In another preferred embodiment, the topical medicament further comprises a chemical trap, wherein the chemical trap is selected from the group consisting of a Diels-Alder trap, an amine trap, a diamine trap, and a thiol trap. In one more preferred embodiment, the Diels-Alder trap is selected from the group consisting of strained alkenes and electron-rich alkenes. In another more preferred embodiment, the Diels-Alder trap is a polymer-supported strained alkene or polymer-supported electron-rich alkene. In another more preferred embodiment, the amine trap is selected from the group consisting of secondary amine such as, but not limited to, 4-amino-2,2,6,6-tetramethylpiperidine-1-oxyl (4-amino-TEMPO), a primary amine such as, but not limited to, a lysine derivative, and an aryl amine, such as, but not limited to, aniline. In another more preferred embodiment, the amine trap is a polymer-supported amine. In another more preferred embodiment the thiol trap is selected from the group consisting of alkyl thiols and aryl thiols such as, but not limited to, a cysteine derivative, tert-dodecane thiol, derivatives of benzyl thiol, furan-2-ylmethanethiol, and derivatives of thiophenol. In another more preferred embodiment, the thiol trap is a polymer-supported thiol. In another more preferred embodiment, the chemical trap is selected from the group consisting of a diamine such as, but not limited to, 1,2-benzenediamine, ethylenediamine, and a polymer-supported diamine, alpha-amino ketone, and alpha-amino imine.

In one embodiment the invention provides a method for detecting, treating, and deactivating alk(en)yl catechols, and/or alk(en)yl resorcinols, wherein the method results in producing a fluorescent compound that fluoresces when illuminated and wherein the fluorescence is induced by photons having a wavelength of between about 250 and 600 nm. In one embodiment the fluorescence can be, for example, between 250 and 300 nm, between 300 and 350 nm, between 350 and 400 nm, between 450 and 500 nm, between 500 and 550 nm, and between 550 and 600 nm. In the alternative, the method results in producing a fluorescent compound that fluoresces when illuminated with light in the visible spectrum and wherein the fluorescence is induced by photons having a wavelength of between about 600 and 750 nm. In one embodiment the fluorescence can be, for example, between 600 and 650 nm, between 650 and 700 nm, and between 700 and 750 nm.

The invention further provides use of a composition comprising an oxidant for the manufacture of an oxidant composition for detecting a catechol, a nitroxide, and a suitable excipient, carrier, or combination thereof. In a preferred embodiment the composition comprises an oxidant in an effective amount for the deactivation of a catechol in poison oak oil.

The invention can be used in a variety of embodiments, for example, for use as chemical sensors and molecular specific deactivating agents. The invention can be used in phototherapy for treatment of an inflammatory response and other disorders. The invention can also be used as a sensor that detects molecules. The invention is of particular use in the fields of clinical diagnosis, clinical therapy, clinical treatment, and clinical evaluation of various diseases and disorders, in the field of consumer goods, for example, over-the-counter medications, balms, ointments, etc., and diagnostic kits, manufacture of compositions for use in the treatment of various diseases and disorders, for use in molecular biology, structural biology, cell biology, molecular switches, molecular circuits, and molecular computational devices, and the manufacture thereof. The invention is also of use in the field of decontamination, whereby equipment contaminated with catechols such as urushiol may be cleansed of contaminant.

In one embodiment, the composition comprises a surface stabilizer. In another alternative embodiment the composition comprises at least two surface stabilizers. In a preferred embodiment, the surface stabilizer is selected from the group consisting of an anionic surface stabilizer, a cationic surface stabilizer, a zwitterionic surface stabilizer, and an ionic surface stabilizer.

In another preferred embodiment, the surface stabilizer is selected from the group consisting of cetyl pyridinium chloride, gelatin, casein, phosphatides, dextran, glycerol, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, dodecyl trimethyl ammonium bromide, polyoxyethylene stearates, colloidal silicon dioxide, phosphates, sodium dodecylsulfate, carboxymethylcellulose calcium, hydroxypropyl celluloses, hypromellose, carboxymethylcellulose sodium, methylcellulose, hydroxyethylcellulose, hypromellose phthalate, noncrystalline cellulose, magnesium aluminum silicate, triethanolamine, polyvinyl alcohol, polyvinylpyrrolidone, 4-(1,1,3,3-tetramethylbutyl)-phenol polymer with ethylene oxide and formaldehyde, poloxamines, a charged phospholipid, dioctylsulfosuccinate, dialkylesters of sodium sulfosuccinic acid, sodium lauryl sulfate, alkyl aryl polyether sulfonates, mixtures of sucrose stearate and sucrose distearate, p-isononylphenoxypoly-(glycidol), decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide; n-noyl β-D-glucopyranoside; octanoyl-N-methylglucamide; n-octyl-β-D-glucopyranoside; octyl β-D-thioglucopyranoside; lysozyme, PEG-phospholipid, PEG-cholesterol, PEG-cholesterol derivative, and PEG-vitamin A.

In another alternative embodiment, the cationic surface stabilizer is selected from the group consisting of a polymer, a biopolymer, a polysaccharide, a cellulosic, an alginate, a nonpolymeric compound, and a phospholipid.

In another alternative embodiment, the surface stabilizer is selected from the group consisting of cationic lipids, polymethylmethacrylate trimethylammonium bromide, sulfonium compounds, polyvinylpyrrolidone-2-dimethylaminoethyl methacrylate dimethyl sulfate, hexadecyltrimethyl ammonium bromide, phosphonium compounds, quarternary ammonium compounds, benzyl-di(2-chloroethyl)ethylammonium bromide, coconut trimethyl ammonium chloride, coconut trimethyl ammonium bromide, coconut methyl dihydroxyethyl ammonium chloride, coconut methyl dihydroxyethyl ammonium bromide, decyl triethyl ammonium chloride, decyl dimethyl hydroxyethyl ammonium chloride, decyl dimethyl hydroxyethyl ammonium chloride bromide, $C_{12-15}$ dimethyl hydroxyethyl ammonium chloride, $C_{12-15}$-dimethyl hydroxyethyl ammonium chloride bromide, coconut dimethyl hydroxyethyl ammonium chloride, coconut dimethyl hydroxyethyl ammonium bromide, myristyl trimethyl ammonium methyl sulphate, lauryl dimethyl benzyl ammonium chloride, lauryl dimethyl benzyl ammonium bromide, lauryl dimethyl(ethenoxy)$_4$ ammonium chloride, lauryl dimethyl(ethenoxy)$_4$ ammonium bromide, N-alkyl $(C_{12-18})$dimethylbenzyl ammonium chloride, N-alkyl $(C_{14-18})$-dimethyl-benzyl ammonium chloride, N-tetradecylidmethylbenzy-1 ammonium chloride monohydrate, dimethyl didecyl ammonium chloride, N-alkyl and $(C_{12-14})$ dimethyl 1-napthylmethyl ammonium chloride, trimethylammonium halide, alkyl-trimethylammonium salts, dialkyl-dimethylammonium salts, lauryl trimethyl ammonium chloride, ethoxylated alkyamidoalkyldialkylammonium salt, an ethoxylated trialkyl ammonium salt, dialkylbenzene dialkylammonium chloride, N-didecyldimethyl ammonium chloride, N-tetradecyldimethylbenzyl ammonium, chloride monohydrate, N-alkyl$(C_{12-14})$ dimethyl 1-naphthylmethyl ammonium chloride, dodecyldimethylbenzyl ammonium chloride, dialkyl benzenealkyl ammoniumchloride, lauryl trimethyl ammonium chloride, alkylbenzyl methyl ammonium chloride, alkyl benzyl dimethyl ammonium bromide, $C_{12}$ trimethyl ammonium bromides, $C_{15}$ trimethyl ammonium bromides, $C_{17}$ trimethyl ammonium bromides, dodecylbenzyl triethyl ammonium chloride, poly-diallyldimethylammonium chloride (DADMAC), dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride, polyquaternium 10, tetrabutylammonium bromide, benzyl trimethylammonium bromide, choline esters, benzalkonium chloride, stearalkonium chloride compounds, cetyl pyridinium bromide, cetyl pyridinium chloride, halide salts of quaternized polyoxyethylalkylamines, quaternized ammonium salt polymers, alkyl pyridinium salts; amines, amine salts, amine oxides, imide azolinium salts, protonated quaternary acrylamides, methylated quaternary polymers, and cationic guar.

In another alternative embodiment, the polymer support for the orthoquinone trap is selected from the group consisting of a polymer, a biopolymer, a polysaccharide, a cellulosic, an alginate, and a phospholipid. In another alternative embodiment, the support may comprise a non-polymeric compound. In another alternative embodiment, the polymer-support for the catalyst for oxidation of the catechol to the orthoquine is selected from the group consisting of a polymer, a biopolymer, a polysaccharide, a cellulosic, an alginate, and a phospholipid.

The invention also provides for a chemical spray that can be used in the field to allow the deactivation of urushiol. In one embodiment the amount of urushiol deactivated is in the range of between about 0.1-100 μg. In a preferred embodiment, the amount of urushiol deactivated is in the range of between about 1-10 μg.

DETAILED DESCRIPTION OF THE INVENTION

Figure 1:
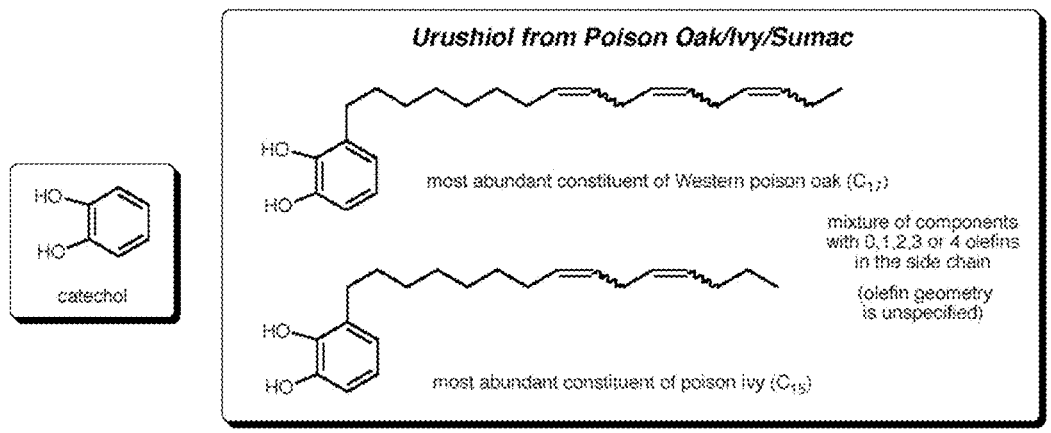
FIG. 1 illustrates the chemical formulae of catechol and exemplary urushiols.

Chemically, urushiol is a name given to a collection of related compounds that are 3-substituted catechols (1,2-benenediols), in which the long hydrophobic chain is a linear $C_{15}$ or $C_{17}$ with 0-4 degrees of unsaturation (see FIG. 1).

Figure 2:
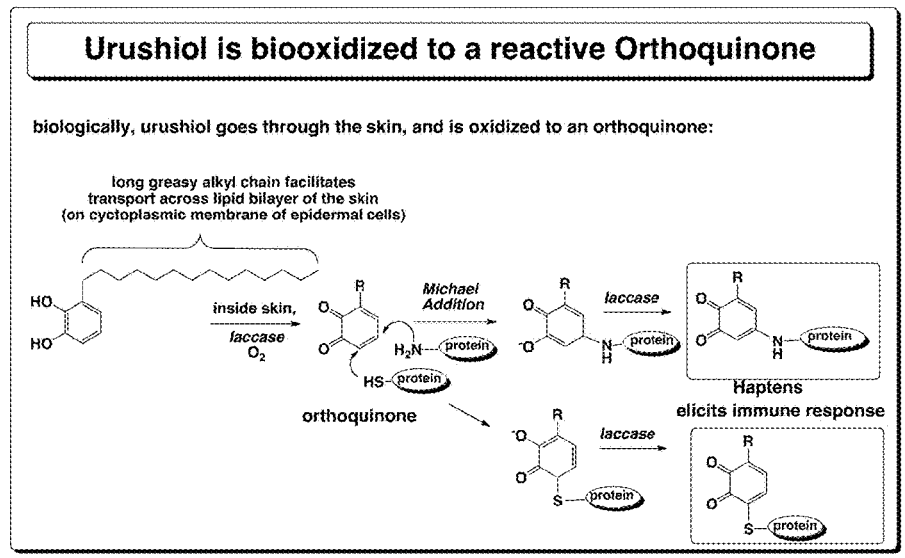
FIG. 2 illustrates how urushiol is bio-oxidized to a reactive orthoquinone.

Biochemically, urushiol transverses the skin, where it is enzymatically oxidized to the orthoquinine, which is then attacked by a nucleophile (amine or thiol residue on a protein) to give the "Michael" addition product (for example, see FIG. 2), which is then enzymatically reoxidized to another orthoquinone: this is the hapten that elicits an immune response, causing contact dermatitis.

In order to deactivate urushiol before it goes through the skin, oxidation to the orthoquinone and trapping will be carried out. This uses a mild oxidant which will not react with the trapping agent. Nitroxides such as TEMPO are shown to catalyze the oxidative conversion of catechols to orthoquinones using air as the stoichiometric oxidant at room temperature. Trapping of the highly reactive orthoquinone is proposed in the presence of air and TEMPO by several different methods.

Figure 3:
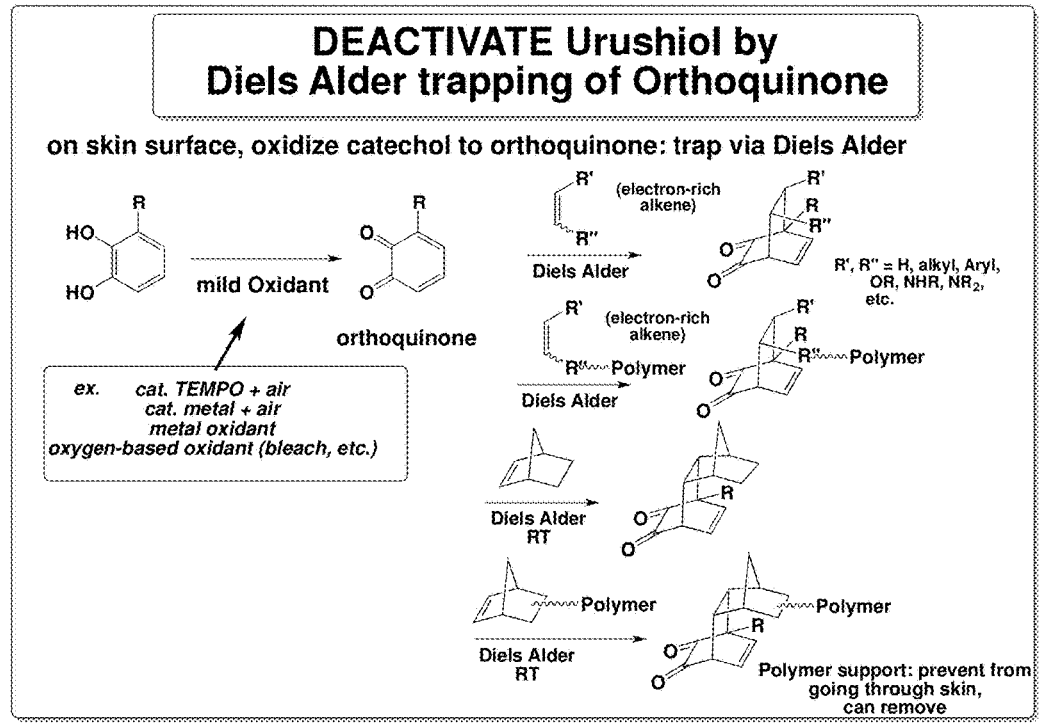
FIG. 3 illustrates how urushiol may be deactivated by Diels-Alder trapping of orthoquinone.
Figure 4:
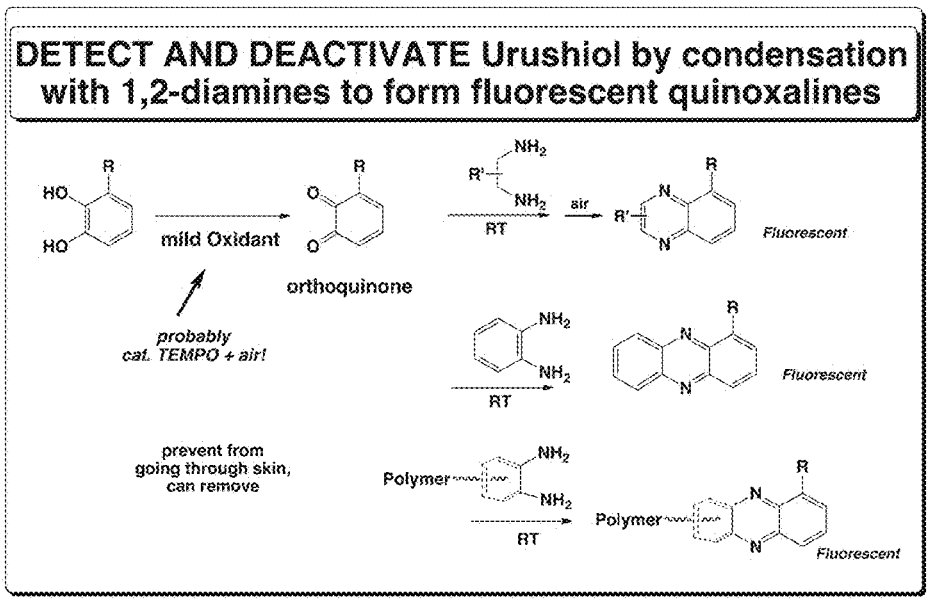
FIG. 4 illustrates how a urushiol may be detected and deactivated by condensation with 1,2-diamines to form fluorescent quinoxalines.
Figure 5:
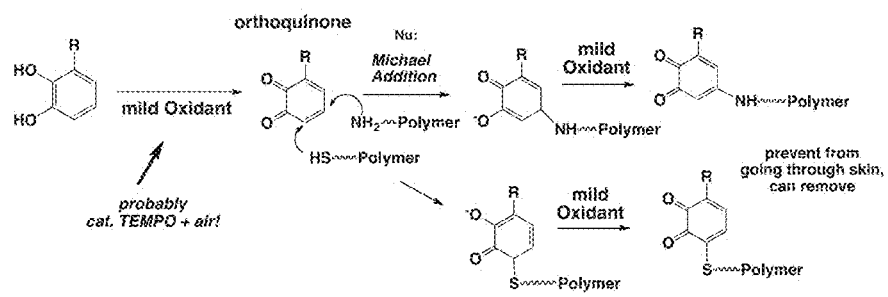
FIG. 5 shows how a urushiol may be deactivated by Michael addition of polymeric nucleophiles to orthoquinone.
Figure 6:
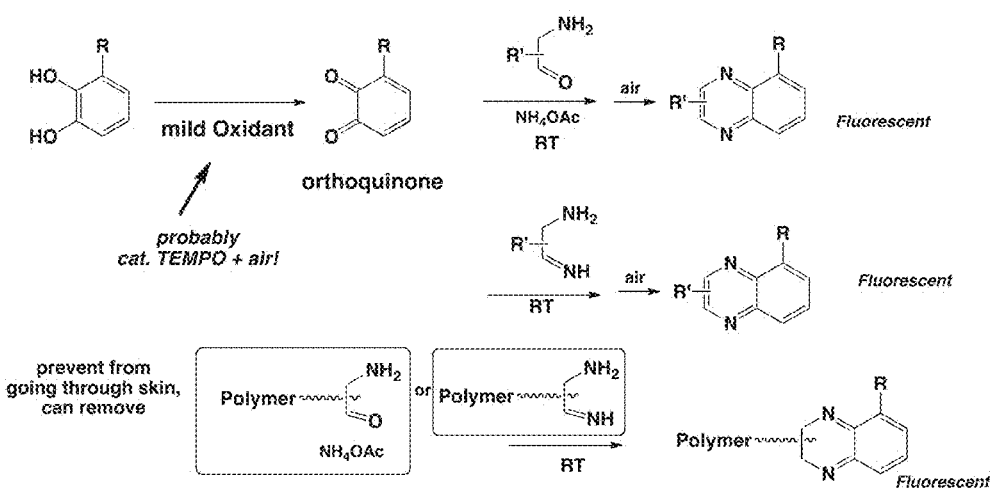
FIG. 6 shows how urushiol may be detected and deactivated by condensation with a-amino ketones/imines to form fluorescent quinoxalines.

1. Diels Alder Reaction with Olefins as shown in FIG. 3. There is precedence in the literature that strained olefins such as norbornenes, and electron rich olefins will undergo Diels Alder reactions with orthoquinones at room temperature. Use of a polymeric norbornene or other olefin trap may also be used.
2. Condensation with 1,2-diamines to form fluorescent quinoxalines as shown in FIG. 4. Condensation of the reactive orthoquinone intermediate with a 1,2-diamine will give a quinoxaline product that is both deactivated and fluorescent, allowing both detection and deactivation of urushiol in one step. Use of a polymeric 1,2-diamine may also be used.
3. Trapping with Nucleophiles in a "Michael" Addition (biomimetic) as shown in FIG. 5. Michael Addition to the reactive orthoquinone intermediate by a nucleophile is a biomimetic reaction. The immediate Michael product will most likely be reoxidized to a new orthoquinone. Use of polymeric nucleophiles may also be used.
4. Condensation with alpha-amino ketones or alpha-amino imines to form fluorescent quinoxalines as shown in FIG. 6. Condensation of the reactive orthoquinone intermediate with an alpha-amino ketone or alpha-amino imine to from a quinoxaline product that is both deactivated and fluorescent, allowing both detection and deactivation of urushiol in one step. Use of the polymeric alpha-amino ketone/imine may also be used.

Best Mode of the Invention

Figure 7:
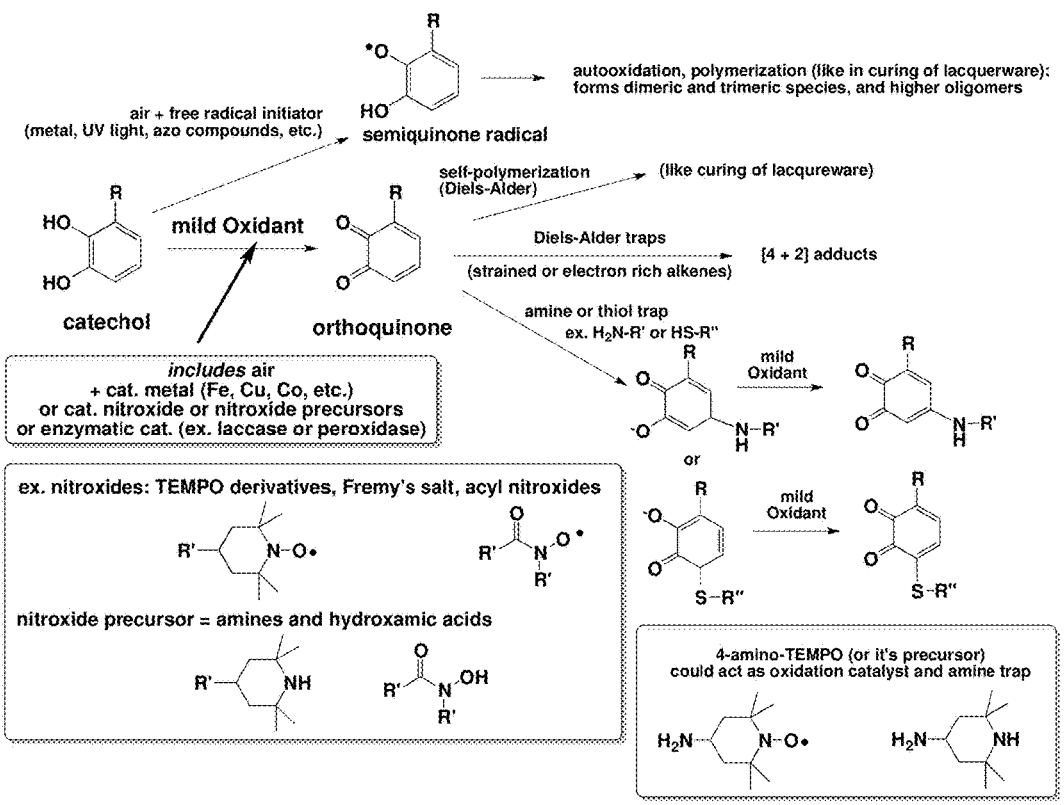
FIG. 7 illustrates an exemplary method for deactivation urushiol by oxidation and subsequent reactions.
Figure 8:
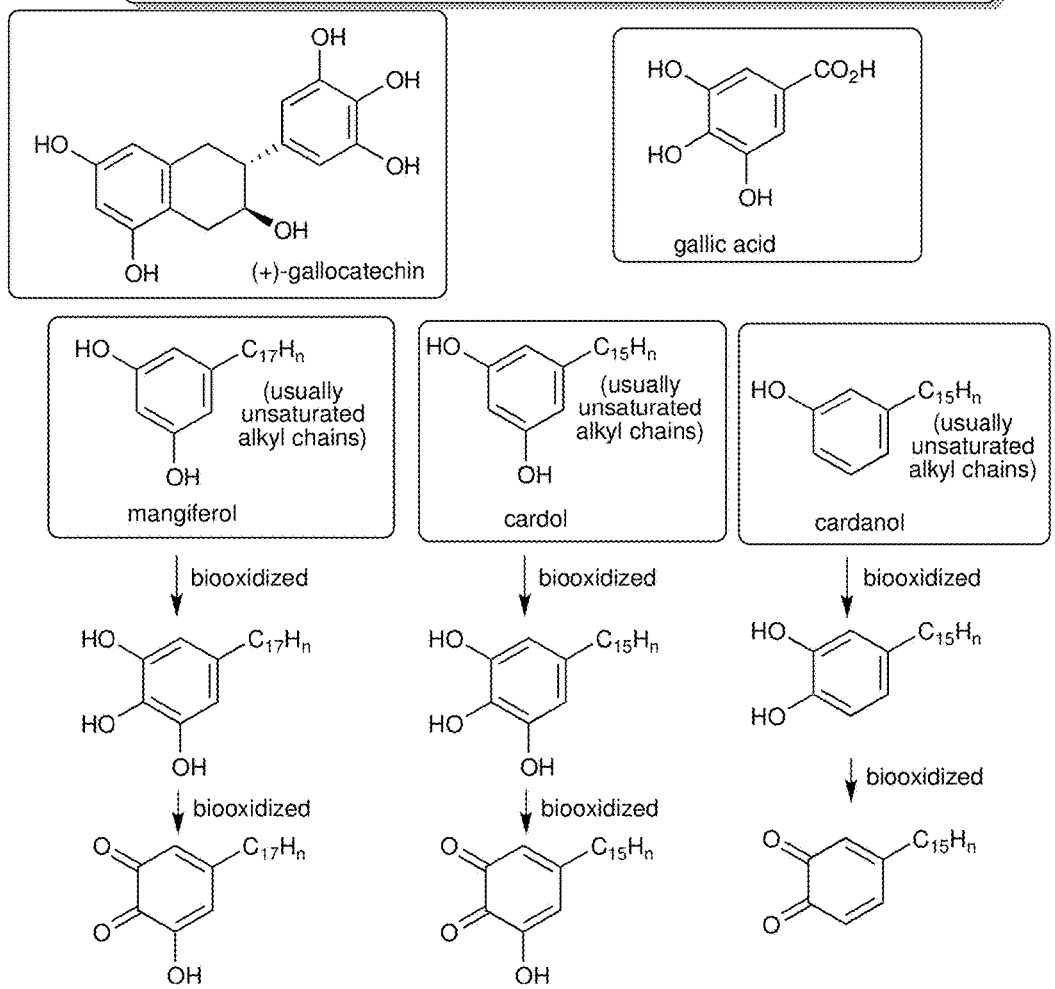
FIG. 8 illustrates representative pyrogallols and catechols commonly found in foods such as red wine, tea, and chocolate: note that compounds 48 and 49 are polyols, and are thus aqueous rather than organic soluble. Also shown is mangiferol (from mango sap), cardol and cardanol (from cashew nut), which are all bio-oxidized to orthoquinones, and can cause contact dermatitis upon exposure to skin.
Figure 9:
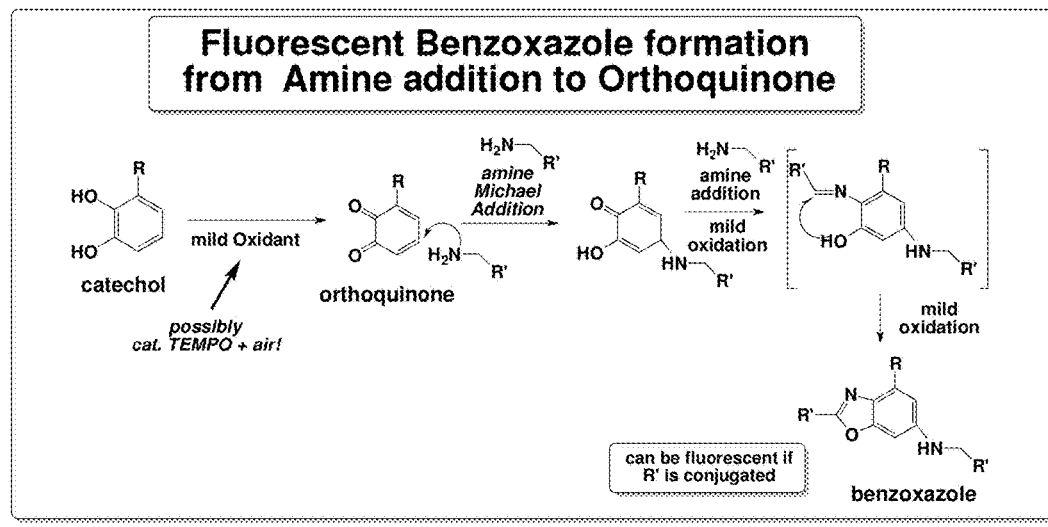
FIG. 9 illustrates reaction of urushiol to an orthoquinone, followed by addition of two equivalents of amine and further oxidation to from a benzoxazole, which can be fluorescent depending on the choice of amine (for example, R'=Ph gives a fluorescent benzoxazole).

In order to deactivate urushiol before it goes through the skin, oxidation and subsequent reaction will convert the catechol functionality into either reactive orthoquinones or semiquinone radicals, which undergo further reactions to prevent the ability of urushiol to result in contact dermatitis. See FIG. 7.

Asian lacquerware is made by polymerization of urushiol: traditionally in a low heat oven in the presence of air. Methods to induce curing (polymerization) of urushiol for lacquerware production include treatment with air plus enzymes or metal catalysts or UV light: these methods can be adopted to deactivate urushiol from poison oak, ivy, and sumac to prevent contact dermatitis under mild conditions.

The mild oxidant may consist of air plus a metal catalyst (such as Fe (such as Fe-salen) Cu or Cobalt or Mn or Ni or Pd or Rh or Ru or Mn or Pt species, in addition to other metals), or an enzyme (such as laccase or peroxidase or tyrosinase or xylanase). Also, nitroxides and air (that is, oxygen) can act as oxidants. Both commercially available nitroxides such as TEMPO derivatives, and the cyclic amine precursors or nitroxides may be used, as oxidation of the amines by air forms nitroxides in small concentration. In another example, the oxidant is selected from the group consisting of bleach, sodium hypochlorite, potassium ferricyanide, hydrogen peroxide, hydroperoxides, dialkyl peroxides, thiourea-hydroperoxide complex, potassium monopersulfate, sodium dichloroisocyanurate, and other solid oxidizers.

For orthoquinone formation, Diels-Alder trapping by strained alkenes (such as norbornadiene), or electron rich alkenes (such as enol ethers, enamines, or styrenes) may trap the species before urushiol can transverse the skin, or self-polymerization can also deactivate the orthoquinone. Nucleophilic trapping by amines or thiols can also trap the orthoquinone to deactivate it. Condensation of the orthoquinone with alpha-amino ketones or alpha-amino imines can also form fluorescent quinoxalines which are both deactivated and trapped.

One particularly attractive option is to utilize 4-amino-TEMPO (or the cyclic amine precursor 4-amino-piperidine-1-oxyl), to serve as both oxidation catalyst and amine nucleophile.

Electron-poor nitroxides are excellent H-atom abstractors: these can react with catechols to form either orthoquinones, or semiquinone radicals, which further undergo oligomerization reactions. Electron poor nitroxides such as acyl nitroxides are easily oxidized from hydroxamic acids: either the pre-formed acyl nitroxides or their precursor hydroxamic acids may be effective. Traditional free radical initiators (azo compounds, di-tert-butyl hyponitrite, peroxides, etc.) may also be effective.

Oxidation by UV-curing can be used to deactivate urushiol on inanimate objects (clothing, tools, fire-fighting equipment, sporting equipment, etc.).

Catechols are a group of compounds well-known to those of skill in the art having diverse biological activities, whilst at the same time being structurally conservative. The invention contemplates that the compositions and methods disclosed herein may be used to detect, inactivate, or bind to any biologically-active catechol composition. In particular the invention contemplates a catechol or other orthoquinone precursor selected from the group consisting of urushiol, catechin, cardanol, cardol, thitsiol, epicatechin, gallocatechin, epigallocatechin, epigallocatechin-3-gallate, and catecholamines epinephrine, norepinephrine, dopamine, and dihydroxyphenylalanine (DOPA). One of skill in the art would consider that the structures of catechols are sufficiently similar that they are a well-known chemical class of compounds.

This can be used as a method to detect the presence of urushiol. As a treatment, transformation of the urushiol into an oxidized and trapped form will prevent transfer through the skin, or prevent bioattachment of a peptide to the orthoquinone inside the skin, preventing oxidation of the catechol and elicitation of an immune response, thus preventing contact dermatitis.

Use of the Compositions for Detection of Urushiol

A composition prepared according to the present invention may be formulated as an aerosol spray, a topical cream, ointment, medicament, or a solution.

An aerosol containing approximately 0.005% to about 5.0% (w/w) of the nitroxide according to the present invention is prepared by dissolving the compositions in absolute alcohol. The resulting solution is then diluted in an organic solvent or purified water, depending upon the hydrophobicity of the compound. Routine experimentation by those having skill in the art can be used to determine an effective amount for detecting a catechol in a sample.

There are several biologically very important catechols: the catecholamines (including epinephrine, norepinephrine, and dopamine), in addition to epicatechin (common in tea). All of these are water-soluble. Water-soluble nitroxides and fluorophores are widely known; nitroxides have been used extensively as an EPR probe in biology. The detection of biologically important catecholamines (including epinephrine, norepinephrine, and dopamine) in aqueous environments could lead to powerful new methods in biomedicine.

Contact dermatitis from exposure of skin to urushiol causes agony and suffering for tens of millions of Americans each year, making this an important human health issue in North America. The invention provides a clear benefit to society, including private outdoors enthusiasts, forestry workers, emergency rescue personnel, military personnel, and others who come in contact with poison oak, poison ivy, or sumac.

In addition, the formulation or aerosol can comprise a solvent, the solvent comprising a polar organic solvent, a non-polar organic solvent, an aqueous solvent, or a non-aqueous solvent.

The invention also provides for a chemical spray that can be used in the field to allow the deactivation of urushiol. In one embodiment the amount of urushiol deactivated is in the range of between about 0.1-100 µg. For example the amount can be 0.1 µg, 0.2 µg, 0.3 µg, 0.4 µg, 0.5 µg, 0.6 µg, 0.7 µg, 0.8 µg, 0.9 µg, 1 µg, 2 µg, 3 µg, 4 µg, 5 µg, 6 µg, 7 µg, 8 µg, 9 µg, 10 µg, 11 µg, 12 µg, 13 µg, 14 µg, 15 µg, 16 µg, 17 µg, 18 µg, 19 µg, 20 µg, 25 µg, 30 µg, 35 µg, 40 µg, 45 µg, 50 µg, 55 µg, 60 µg, 65 µg, 70 µg, 75 µg, 80 µg, 85 µg, 90 µg, 95 µg, or 100 µg. In a preferred embodiment, the amount of urushiol deactivated is in the range of between about 1-10 µg. For example the amount can be 1 µg, 2 µg, 3 µg, 4 µg, 5 µg, 6 µg, 7 µg, 8 µg, 9 µg, or 10 µg.

The invention will be more readily understood by reference to the following examples, which are included merely for purposes of illustration of certain aspects and embodiments of the present invention and not as limitations.

EXAMPLES

Example I

Synthesis and Development of the Components of the Deactivation Method: Optimize the Selection of the Oxidant and/or Catalyst to Effect Oxidation of the Catechol (or Phenolic Precursor) to the Orthoquinone, Optimize the Choice of Orthoquinoe Trap, and Whether any or all Components Will be Polymer-Supported In the case of a nitroxide catalyst for oxidation, the chemical design of the nitroxide can be explored, entailing the choice of the optimum nitroxide and tether to prepare a robust, soluble and effective component for this deactivation system. The six-membered ring TEMPO is by far the most common nitroxide scaffold, however there are a number of other common stable nitroxide classes. Considerations in optimization of the nitroxide structure include ease and cost of synthesis, versatility in designing and optimizing the tether between the nitroxide if attached to a polymer, stability and solubility. Common stable nitroxide classes include TEMPO (tetramethylpiperidinyl-1-oxyl), proxyl (pyrrolidine analogues), nitronyl, imino and doxyl nitroxides. The inventor and the inventor's research laboratory has been engaged in the synthesis and applications of nitroxides for over a decade, thus has extensive experience in the synthesis of new nitroxides. In addition, a large number of commercially nitroxides are available from Toronto Research Chemicals, Inc. (North York, Canada).

Example II

Optimizing the Detection System with Regard to Stoichiometry, Solvent, Concentration, Reaction Time, and Compatibility with Skin or Inanimate Object Application Time and effectiveness in deactivating the bulk of urushiol is explored. As exposure to 0.001 mg of urushiol can elicit allergic contact dermatitis, very small amounts of urushiol should to be deactivated to make this method effective. The optimal stoichiometry to obtain a short reaction time and complete deactivation is needed.

The use of other mild oxidants that will rapidly oxidize hydroxylamine to nitroxide in organic solvents, but not oxidize catechol to quinone, are investigated. Particularly attractive are iron salts as less toxic alternatives to copper.

References

Bobko A A, Kirilyuk I A, Grigor'ev I A, et al., *Free Radical Biology and Medicine* 2007 Volume: 42 Issue: 3 Pages: 404-412.

O. Vogl, Edward C. Taylor *J. Am. Chem. Soc.,* 1959, 81 (10), pp 2472-2474; DOI: 10.1021/ja01519a047

Tsujimoto, T.; Uyama, H.; Kobayashi, S., Synthesis and curing behaviors of cross-linkable polynaphthols from renewable resources: Preparation of artificial urushi. *Macromolecules* 2004, 37 (5), 1777-1782.

Xia, J. R.; Xu, Y. L.; Hu, B. H.; Lin, J. H., A rapid approach to urushiol-copper(I) coordination polymer under UV irradiation. *Progress in Organic Coatings* 2009, 65 (4), 510-513.

Kaizer, J.; Barath, G.; Csonka, R.; Speier, G.; Korecz, L.; Rockenbauer, A.; Parkanyi, L., Catechol oxidase and phenoxazinone synthase activity of a manganese(II) isoindoline complex. *Journal of Inorganic Biochemistry* 2008, 102 (4), 773-780.

Harigaya, S.; Honda, T.; Rong, L.; Miyakoshi, T.; Chen, C. L., Enzymatic dehydrogenative polymerization of urushiols in fresh exudates from the lacquer tree, *Rhus vernicifera* DC. *Journal of Agricultural and Food Chemistry* 2007, 55 (6), 2201-2208.

Tsujimoto, T.; Ando, N.; Oyabu, H.; Uyama, H.; Kobayashi, S., Laccase-catalyzed curing of natural phenolic lipids and product properties. *Journal of Macromolecular Science Part a—Pure and Applied Chemistry* 2007, 44 (7-9), 1055-1060.

Muller, G. H.; Waldmann, H., An enzyme-initiated domino hydroxylation-oxidation-carbo-Diels-Alder reaction cascade. *Tetrahedron Letters* 1996, 37 (22), 3833-3836.

Kaizer, J.; Pap, J.; Speier, G., Modeling antioxidant properties of polyphenols by the TEMPO-initiated reaction of 3,5-di-tert-butylcatechol with dioxygen. *Food Chemistry* 2005, 93 (3), 425-430.

Warrener, R. N.; Johnston, M. R.; Schultz, A. C.; Golic, M.; Houghton, M. A.; Gunter, M. J., Direct formation of alpha-dione BLOCKs from o-benzoquinone cycloadditions and their value in the synthesis of fused quinoxalines, 1,10-phenanthrolines and pteridines. *Synlett* 1998, (6), 590-+.

Hernandez-Juan, F. A.; Cockfield, D. M.; Dixon, D. J., Enantioselective organocatalytic aryloxylation of aldehydes with o-quinones. *Tetrahedron Letters* 2007, 48 (9), 1605-1608.

Xu, D. W.; Chiaroni, A.; Fleury, M. B.; Largeron, M., Electrochemically induced cascade reaction for the assembly of libraries of biologically relevant 1,4-benzoxazine derivatives. *Journal of Organic Chemistry* 2006, 71 (17), 6374-6381.

Xia, J. R.; Lin, J. H.; Xu, Y. L.; Chen, Q. H., On the UV-Induced Polymeric Behavior of Chinese Lacquer. *Acs Applied Materials & Interfaces* 2011, 3 (2), 482-489.

Those skilled in the art will appreciate that various adaptations and modifications of the just-described embodiments can be configured without departing from the scope and spirit of the invention. Other suitable techniques and methods known in the art can be applied in numerous specific modalities by one skilled in the art and in light of the description of the present invention described herein. Therefore, it is to be understood that the invention can be practiced other than as specifically described herein. The above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

I claim:

1. A method for deactivating a catechol in a sample, the method comprising the steps of (i) contacting an oxidant and a catalyst with the sample, wherein the catalyst is a nitroxide, (ii) allowing the oxidant to react with the catechol in the sample thereby creating an orthoquinone; (iii) allowing the orthoquinone to react with the oxidant thereby generating a polymer; the method resulting in deactivating the catechol in the sample.

2. A method for deactivating a catechol in a sample, the method comprising the steps of (i) contacting an oxidant and a catalyst with the sample, wherein the catalyst is a nitroxide precursor, (ii) allowing the oxidant to react with the catechol in the sample thereby creating an orthoquinone; (iii) allowing the orthoquinone to react with the oxidant thereby generating a polymer; the method resulting in deactivating the catechol in the sample.

3. The method of claim 1, wherein the nitroxide is selected from the group consisting of alkyl nitroxide, Fremy's salt, and acyl nitroxide.

4. The method of claim 1, wherein the nitroxide is tetramethylpiperidinyloxy (TEMPO).

5. The method of claim 2, wherein the nitroxide precursor is selected from the group consisting of an amine and a hydroxamic acid.

6. The method of claim 1, the method further comprising the steps of (iv) providing a free radical initiator, (v) allowing the orthoquinone to react with the free radical initiator, thereby generating a semiquinone radical, (vi) allowing the semiquinone radical to auto-oxidize, or (vii) allowing the semiquinone to polymerize, the method resulting in deactivating the orthoquinone.

* * * * *